United States Patent [19]

Huffman

[11] Patent Number: 4,734,033
[45] Date of Patent: Mar. 29, 1988

[54] FLEXIBLE DENTAL MODEL ARTICULATOR

[75] Inventor: Ronald E. Huffman, Tucson, Ariz.

[73] Assignee: KV33 Corporation, Tucson, Ariz.

[21] Appl. No.: 9,232

[22] Filed: Jan. 30, 1987

[51] Int. Cl.⁴ ............................................. A61C 11/00
[52] U.S. Cl. ........................................ 433/60; 433/63; 433/64
[58] Field of Search ................................. 433/60, 54

[56] References Cited

U.S. PATENT DOCUMENTS 3,466,750  9/1969  Timberlake et al. ................. 433/54
4,533,323  8/1985  Huffman ............................... 433/60

Primary Examiner—Robert Peshock
Attorney, Agent, or Firm—Harry M. Weiss & Assoc.

[57] ABSTRACT

An articulator for casts of a dental model correlates the casts with the condition to be redintegrated throughout a full range occlusal and masticatory registration. The articulator includes hinged mirror image flexible brackets; each bracket has a base and arms of nonuniform cross section to encourage localized flexure of the brackets. Each base of the brackets supports a sphere to be positioned within a respective mounting attached to each cast. Each of the spheres may include at least a partially circumferential groove for distributing by capillary action or wicking an adhesive intermediate the sphere and the engaged cavity to secure the articulator to the casts after alignment of the paired casts. Simulating and tracing the paths of natural occlusal and masticatory registration is effected by pivotal movement about the hinge line between the brackets and flexing of the brackets forming the articulator.

25 Claims, 10 Drawing Figures

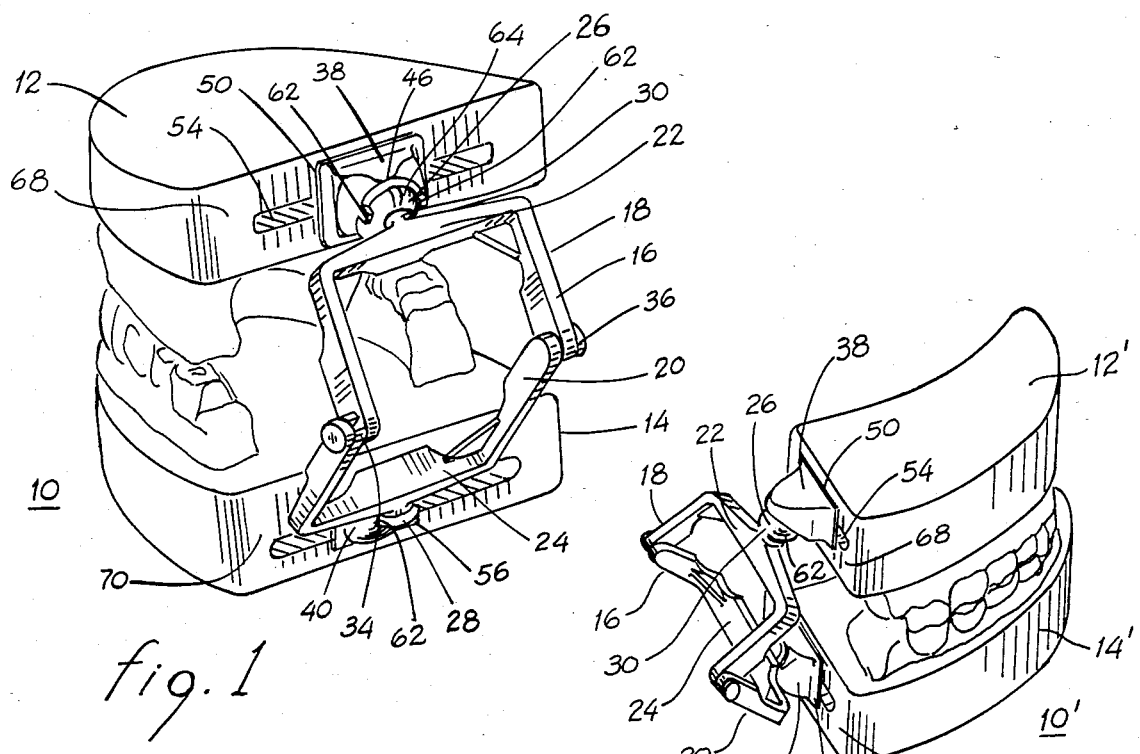
fig. 1
fig. 2
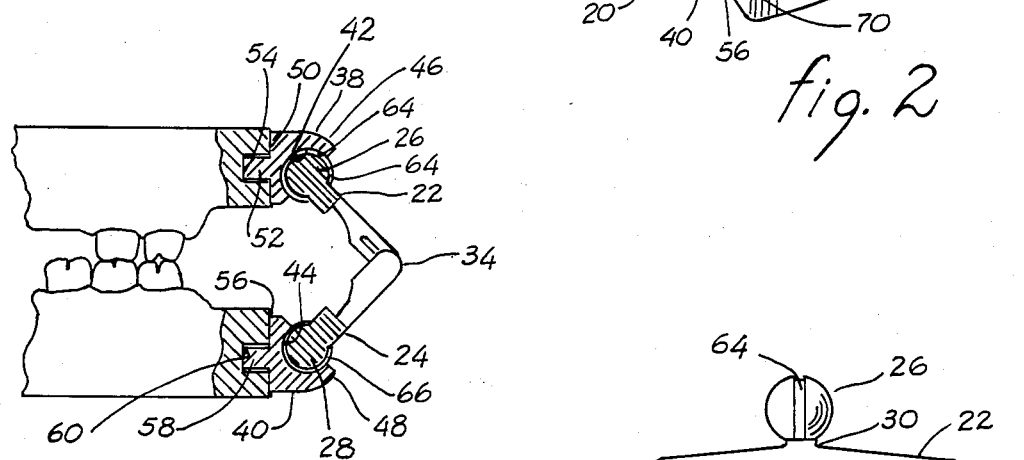
fig. 3
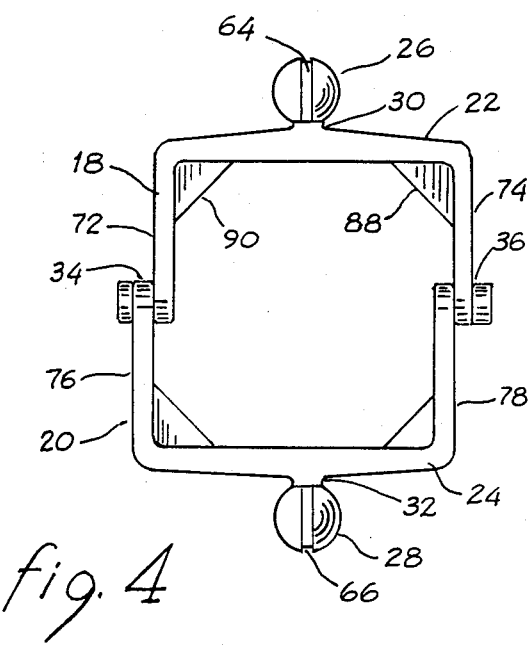
fig. 4

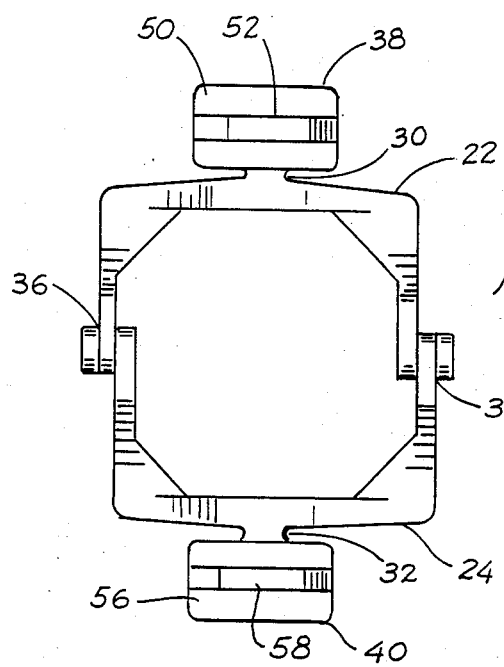
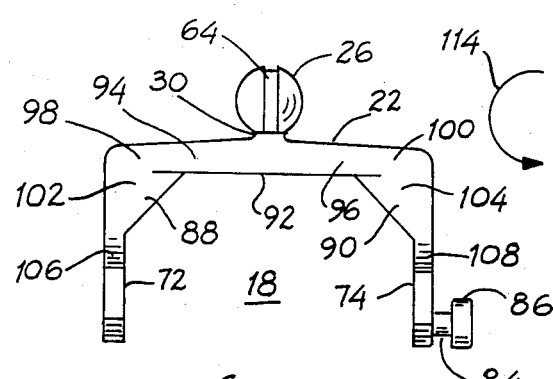
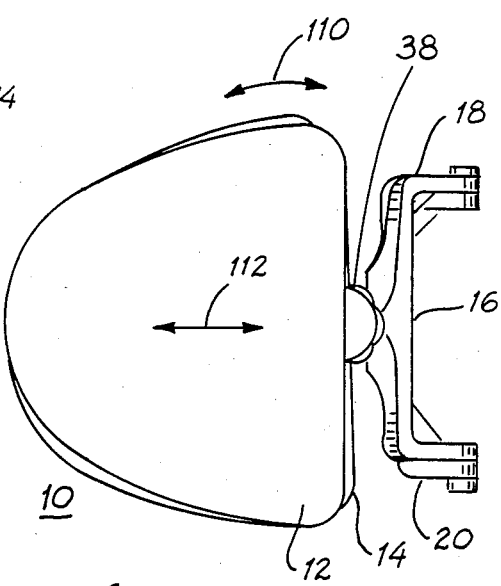
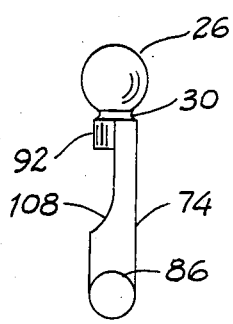
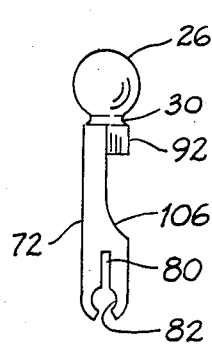
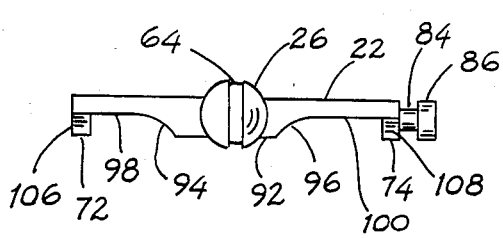

FLEXIBLE DENTAL MODEL ARTICULATOR

RELATED U.S. PATENS AND APPLICATIONS

The present application is directed to an improvement over the articulators described in the U.S. Patents: U.S. Pat. Nos. 4,382,787 entitled "DENTAL MODEL ARTICULATOR"; 4,449,930, entitled "DENTAL MODEL ARTICULATOR"; 4,533,323 entitled "MOUNTING FOR DENTAL MODEL ARTICULATORS"; 4,533,581 entitled "DENTAL MODEL ARTICULATOR"; Des. 286,179, entitled "DENTAL ARTICULATOR WITH BALL MOUNTING"; Des. 286,436, entitled "DENTAL ARTICULATOR WITH A TAB MOUNTING"; and, application for patent entitled "DENTAL ARTICULATOR WITH A FLAT PLATE MOUNTING", Ser. No. 574,228; all of which are assigned to the present assignee.

TECHNICAL FIELD

The present invention is related to dental articulators for use with dental model casts.

BACKGROUND ART

Correlators or articulators for use with casts of a dental model to develop prosthetic dentures or denture elements have been used for a number of years. These articulators range from a very simple device affording only fixed pivotal movement between a pair of casts of highly sophisticated and mechanically complex devices which are capable of simulating the full range of occlusal and masticatory registration unique to any patient. The relatively simple devices are generally inadequate to provide sufficiently accurately registered prosthetic restoration to avoid extensive visits with a dentist to obtain adjustments thereof while the very complex devices are time consuming to operate and require extensive training to use properly. In either situation, the costs incurred to the patient are substantial. Moreover, none of the prior art articulators permit disengagement of the casts from registration with one another without extensive realignment upon reengagement. Thus, a technician is usually forced to perform his work while the casts are mounted on the articulator. Such an environment is difficult to work in with speed and accuracy.

Each of the following listed U.S. patents are directed to dental articulators which incorporate lockable ball and socket elements to afford pivotal movement and extensible members to afford translational movement; U.S. Pat. Nos. 175,046, 530,524, 537,812, 565,326, 981,430, 1,736,006, 1,841,729, 2,571,280, 2,600,899, 2,608,762, 2,621,407, 2,765,533, 4,1,69,314, 4,196,518 and Belgian Pat. No. 572,850.

An articulator which provides structure to effect a simple hinged movement without provision of mechanical structure for defining translatory movement of multi-axis pivotal movement is disclosed in U.S. Pat. No. 2,430,177. Simulation of the full range of occlusal and masticatory registration is obtained by resiliently flexing the articulator. Such resiliency is afforded by the coil spring like configuration of a wire element defining each leg of two pairs of legs. For a well trained and experienced technician, the freedom of movement afforded by this articulator is sufficient to permit the formation and adjustments of most prosthetic dentures. Accurate use of the device is predicated upon the formation of elongated sockets within each cast of a dental model for receiving, capturing and retaining each of the four wire legs. The casts usually vary in overall physical size, depending upon the size of the patient's teeth to be simulated and the size and configuration of the base formed. To employ the articulator described in this patent, uniformity of spacing during formation of the casts is time consuming and requires an experienced technician. No adjustment capability exists within the articulator itself to accommodate differences in spacing, as would be expected, as the size of a pair of casts vary in proportion to the physical size of the patient's jaws and the usually uniquely sized bases therefor. Other U.S. Patents describing articulators include U.S. Pat. Nos. 824,096, 3,429,045 and 3,466,750.

All of the articulators described in the various patents enumerated above are primarily intended to be reused. Such reuse requires dismantling of the model dental casts therefrom, clean up of the articulators in preparation for reuse and periodic maintenance and repair; all of which activities are time consuming and contribute to overhead costs. Moreover, a substantial investment in articulators must be made in order to have sufficient stock of articulators to accommodate the rate of use, turnaround time and loss/damage rate.

DISCLOSURE OF THE INVENTION

The present invention is directed to an inexpensive throw away articulator for dental models. The articulator includes a pair of brackets of flexible resilient material interconnected by snap fit hinges. A sphere is disposed at opposed ends of each pair of brackets. One of these spheres is locatable in a cavity formed in a mounting attached to each cast. Upon alignment of the casts with one another and development of the respective cavities, each sphere is adhesively attached within its respective cavity and the casts become hingedly attached to one another through the pair of brackets. To ensure flow of the adhesive adjacent a substantial part of the common surface area between each sphere and its cavity, a partially circumferential groove may be formed in each sphere. The groove aids in distributing the adhesive by promoting flow through capillary and wicking action. Simulating the full range of natural occlusal and masticatory registration is effected by a combination of pivotal movement about the hinge line and flexing of the respective brackets. Use of the snap fit hinge embodiment permits rapid disassembly and reassembly without the need of realignment to effect proper registration between the casts; accordingly, a technician can readily perform his work on each of the casts or dental restoration in comfort by placing the cast to be worked upon on a work surface or a holder.

The reduced cross section of each bracket of the pair of brackets proximate the junction between the base member and each of the arms, in combination with the web therebetween and the greater depth than width of the remaining portions of the base member and the arms, assists in focusing the major flex of the brackets at such junctions to assist and render more facile the simulation of the full range of occlusal and masticatory registration unique to the articulated dental model without modification or change of the alignment between the casts.

A primary object of the present invention is to provide apparatus for operatively simulating the occlusal and masticatory relationships to be redintegrated in a dental model.

Another object of the present invention is to provide apparatus for mounting and flexibly holding casts of a dental model to simulate their natural registration to facilitate precise occlusal and masticatory correlation of a dental restoration.

Still another object of the present invention is to provide a flexible articulator for resiliently associating operatively interconnected spaced dental model casts for relative adjustment thereof throughout the range of a full spherical orbit.

Yet another object of the present invention is to provide an articulator having a localized flexure for dental models which is simple and inexpensive to manufacture and operable throughout a wide range of relative adjustments.

A further object of the present invention is to provide a throw away flexible articulator readily attachable to paired dental model casts which provides a wide range of alignment therebetween.

A yet further object of the present invention is to provide a two piece dental articulator, the two pieces of which promote flexing at mirror image locations.

A still further object of the present invention is to provide an articulator of mirror image flex controlled brackets for supporting a pair of casts, which articulator can be disassembled by disengaging snap fit pivots and assembled without need for realignment of the casts by engaging the snap fit pivots.

These and other objects of the present invention will become apparent to those skilled in the art as the description thereof proceeds.

BRIEF DESCRIPTION OF THE DRAWINGS

The present invention may be described with greater specificity and clarity with reference to the following drawings, in which:

FIG. 1 is a perspective view illustrating the articulator supporting a pair of full base casts of a dental model;

FIG. 2 is a perspective view illustrating the articulator supporting a pair of quadrant base casts of a dental model;

FIG. 3 is a partial cross sectional view illustrating the articular attached to the casts of a dental model;

FIG. 4 is a rear view of the interconnected brackets of the articulator;

FIG. 5 illustrates the mountings securable to the articulator;

FIG. 6 is a front view of one of the brackets;

FIG. 7 is a top view of one of the brackets;

FIG. 8 is a left side view of one of the brackets;

FIG. 9 is a right side view of one of the brackets; and

FIG. 10 illustrates simulation of the full range of occlusal and masticatory registration of the dental model by flexing of the articulator.

BEST MODE OF CARRYING OUT THE INVENTION

In the practice of prosthetic dentistry, one very important techincal problem is the shaping and fitting of the restoration occlusal surfaces to register, meet and operatively cooperate with opposed surfaces in conformity with the established habits, idiosyncrasies and tooth facet inclinations of the user. These many factors peculiar to the individual have heretofore made proper operative correlation of the restoration with the associated dental elements almost invariably a matter susceptible of satisfactory resolution only through repetitious adjustments and modifications had in the dental chair after installation of the restoration. This occurs despite the use of fixed, even though adjustable, mechanically simulated axes of articulation, planes and arcs of occlusion, lines, planes and axes of symmetry and the like which fail to provide the full orbital range necessary for reconstitution of the natural dental relationships determinable from the traces and indices upon and established through use of the original dentures. To facilitate attainment of the desired operative registration between restorations and their associated dental elements and corrections in the dental chair, the present invention provides a device for laboratory use wherein the relationships to be redintegrated can be fully and accurately portrayed and operatively duplicated as a check mounting for the restoration.

The present invention is a device which hingedly, yieldably and separably associates for registration a pair of casts of a dental model in spaced opposition and throughout a full spherical orbit wherein every phase and condition of dental occlusive attitude may be exemplified.

In practice, the casts of both the upper and lower natural dentures along with the conditions thereof requiring restoration or correction are made by well known techniques. The casts are secured to the present invention to register in simulation of the natural relationships they portray when positioned in a substantially parallel relationship at one limit of the range of relative movement, which position is determinable by the structure of the invention. Through the novel features, structure and characteristics of the invention correlating restoration or correction and the facet disposition and inclination thereof with the operative range and pattern of movement of the original dentures becomes possible.

Referring to FIG. 1, there is shown a complete full base dental model 10 having a pair of mating dental model casts 12 and 14 simulative of the original dentures and the condition requiring restoration or correction. FIG. 2 illustrates a complete quadrant base dental model $10^1$ having a pair of mating dental model casts $12^1$ and $14^1$ simulative of the original dentures and the condition requiring restoration or correction. An articulator 16 is attached to the casts of either or each of dental models 10 and $10^1$, as illustrated. The articulator maintains the casts positionally simulative of the natural relationships portrayed when substantially in parallel relationship at one limit of the range of relative movement. The articulator includes a pair of interconnecting elements or brackets 18 and 20 pivotally attached to one another and of resilient flexible material sufficient to accommodate relative movement about all axis and within all planes between the casts in either and each dental model in simulation of the operative range and pattern of the original dentures.

Referring jointly to FIGS. 3, 4 and 5, further details of articulator 16 will be described. Each of brackets 18 and 20 includes a base member (22,24), each of which base members supports a ball or sphere (26, 28). Each sphere may extend directly from its respective bracket or one or both of the spheres may be supported upon a straight or angled staclk (30,32) extending from the respective bracket. Brackets 18 and 20 are pivotally joined to one another by pivot means 34, 36; preferably, the pivot means is of the snap fit type, as illustrated.

To mount articulator 16, mounting means 38 and 40 are attached to the rear faces of the respective casts. Each mounting means includes a semi-spherical or partially spherical depression disposed at the respective extremity. In example, mounting means 38 includes depression 42 and mounting means 40 includes depression 44. Which depressions are sized to mate with spheres 26, 28. Spheres 26 and 28 are located within their respective depressions 42, 44 upon angular adjustment of the respective brackets to obtain the requisite spatial relationship therebetween; nominally, the brackets when joined, define an interior obtuse angle. To maintain the casts in the predetermined fixed spatial relationship to one another at one limit of the range of relative movement, an adhesive is applied intermediate the spheres and their respective depressions to fixedly secure the respective bracket in fixed angular orientation with respect to the mounting means. Pivotal movement of the casts is effected by relative angular displacement between the joined brackets about the respective pivot means or hinged line. Translational movement in any plane and rotational movement about any axis of the casts with respect to one another is accommodated by the flexibility of brackets 16 and 18.

With the above general understanding of the basic function and structure of the invention, it may be beneficial to review and analyze certain nuances of the invention which render it of great practical benefit in the field of dental correction and restoration.

Each of mounting means 38 and 40 may be generally triangular in one plane to provide an apex (46, 48) within which a depression (24, 44) is formed. Base 50 of mounting means 38 may include a ridge or tab 52 for mechanical engagement with a slot 54 formed in the rear surface of cast 12. Base 56 of mounting means 40 includes tab 58 for engagement with slot 60 of cast 14. The resulting mechanical engagement, in combination with mastic or adhesive disposed therebetween, rigidly secures each mounting means to its respective cast.

During initial alignment and attachment of the brackets to the mounting means, maintenance of the casts in a predetermined relationship is critical. To simplify the manipulation during attachment, retaining fingers 62 extend from apex 46. These fingers are of resilient material and, in the quiescent state, cant toward one another to provide snap retention for sphere 26 inserted within depression 42. Similar fingers 62 extend from apex 48 of mounting means 40 to engage sphere 28. With the use of such fingers, articulator 16 is retained in place during positioning of casts 12 and 14 and the need for manually retaining the articulator in place during such orientation of the casts is obviated. Upon achievement of the orientation of the casts, an adhesive, such as any one of the commercially available fast setting cyanoacrylate, aerobic or aerobic adhesives, may be employed to secure each sphere within its respective depression.

To facilitate and promote flow of adhesive intermediate the common surfaces of each sphere and its receiving depression, a groove (64, 66) extending partially circumferentially about each sphere (26,28) is formed. For best results, the groove in each sphere extends sufficiently about the sphere to have an end exposed irrespective of the angular orientation of the partially sphere enclosing mounting means. Upon application of a drop of the adhesive upon the sphere, the adhesive will flow along the edge of the depression and, by capillary or wicking action, will flow intermediate the adjacent opposing surfaces of the sphere and depression. The extent of flow is a function of the spacing therebetween provided and the viscosity of the adhesive. The groove promotes flow of adhesive from either and both ends along its full covered length due to capillary action. Moreover, flow of adhesive lateral of the groove intermediate the opposing surface of the depression and sphere will also occur due to capillary action and wicking. The resulting bond formed upon curing of the adhesive extends essentially circumferentially about the opening of the depression and essentially along an arc into the depression, which arc may subtend an angle of approximately 180 degrees. Furthermore, some or all of the opposing spherical surface area common to both the depression and the sphere may become bonded to one another. The strength of the resulting bond has been found by testing to be greater than the fracture strength of the articulator and mounting means when they are made of plastic.

Alternatively, a mounting may be defined by a cylindrical cavity (not shown), such as may be formed by a conventional drill bit, or a partial spherical cavity, such as may be formed by a ball burr developed in rear faces 68, 70 of casts 12, 14 respectively. Spheres 26 and 28 may be located within their respective cavities upon angular adjustment about the pivot axis of the respective brackets to obtain the requisite spatial relationship therebetween. To maintain the casts in the predetermined fixed spatial relationship to one another at one limit of the range of relative movement, an adhesive is applied intermediate the spheres and their respective cavities to fixedly secure the respective bracket in fixed angular orientation with respect to the casts. By having the spheres grooved, as described above, the adhesive bond formed in essentially commensurate with the opposed surface areas of the sphere and cavity for reasons stated above.

Articulator 16, as illustrated primarily in FIG. 4, is formed of a pair of mirror image brackets, each of which includes a base member (22,24) and a pair of arms (72, 74 and 76, 78). Each base member supports a sphere (26, 28), which sphere may be, but is not necessarily, located laterally off set of the longitudinal axis of its respective base member and off center along the longitudinal axis such that upon mating of the brackets, a line drawn through the center of the spheres is orthogonal to a line representative of the pivot axis of the articulator. The extent of longitudinal offset of the spheres (26, 28) is a function of the dimensions attendant the pivot means (34, 36). That is, upon mating of the brackets at the pivot means, one bracket is offset from the other and the extent of offset is a function of the width of the arms (72, 74, 76, 78) at the pivot means. More particularly, sphere 26 is offset along base member 22 toward arm 72 by an amount equivalent to the width of arm 72 and sphere 28 is offset along base member 24 toward arm 78 by an amount equivalent to the width of arm 78. As arms 72 and 78 are duplicative of one another, the offset of each of spheres 26 and 28 is the same and both spheres lie upon a common line orthogonal to a line extending through the pivot axis upon attachment of the brackets to one another. As illustrated, the lateral offset and/or displacement from the base member of each sphere may be effected by a supporting stalk (30, 32). Such stalk also has the further benefit of increasing the distance between the respective base member and the rear face of the attached cast to prevent interference therebetween on attachment and use of the articulator.

FIGS. 6, 7, 8 and 9 illustrate one bracket (18), which bracket is duplicative of the other bracket (20) and the brackets are mirror images of one another. The arms of each bracket may be formed to include complementary elements to establish the pivot means. In example, one arm may include a slot 80 having a circular bearing surface 82 disposed along the slot. The other arm may include a pin 84 extending therefrom for retentative engagement with a corresponding slot and bearing surface. The pin, molded or otherwise formed upon fabrication of each of brackets, may be a simple shaft extending therefrom and terminated by an end plate 86. The space intermediate the arm and end plate is generally equivalent to the width of the arm to be disposed therebetween in slotted retention upon the shaft. Alternatively, each arm may include an aperture penetrably engagable by ancillary pin means or the like. Webs 88, 90 or other strengthening means may be employed at the interconnection between the base member and the extending arms to provide the requisite strength, yet minimize the mass and size of the articulator.

Preferably, the pivot means is of the snap fit type such that disengagement and reengagement of the brackets (and the supported casts) may be readily effected. Upon reengagement, the casts will be in registration with one another as no adjustments or parameters affecting registration are disturbed by disengagement/reengagement of the pivot means.

In a variant of articulator 16, the pivot means interconnecting the brackets is a flexible resilient membrane formed as part of the joined arms of the brackets. As noted above, each of the brackets are of flexible resilient material to permit manipulation of the casts through every phase and condition of dental occlusive attitude. And, the integrally formed joining membranes, being of substantially reduced thickness than the interconnected arms, serve in the nature of a hinge to permit pivotal movement of the brackets and attached casts relative to one another.

To focus the flexing of the brackets (18, 20) upon predetermined portions of the base members and the arms, the cross sections of the base members and the arms are non uniform along their respective lengths. The varying cross sections will be described with particular reference to FIGS. 6, 7, 8 and 9. Base member 22 is of approximately equal height and depth at its center section 92, which center section supports sphere 26 directly or via stalk 30. The height of the center section may taper toward the opposed ends with an uniform or nonuniform taper. In one embodiment, the depth of the base member is substantially reduced by the employment of curved surfaces 94, 96 to a depth at opposed end portions 98, 100, to half of that attendant center section 92. Surfaces 102, 104 of webs 88, 90, respectively, are essentially coincident with an extension of the surfaces of opposed end portions 98, 100. The opposite surfaces of the webs are recessed from the corresponding lateral sides of the base member and the arms, as illustrated in FIG. 4.

Arms 72, 74 have a width throughout their length of approximately that of the depth of opposed end portions 98, 100 of the base member. The depth of the arms attendant therein respective junctions with the base member is approximately the same as the width of the arms. However, the depth of the arms is increased by a factor of approximately two toward the pivot means and the change in depth is coincident with and formed by curved surfaces 106, 108. It may be noted that the thickness of webs 88, 90 toward the ends of the respective arms may increase coincident with the increasing depth of the arms as defined by surfaces 106, 108, respectively.

With the construction of brackets 18, 20 as depicted in FIGS. 6, 7, 8 and 9, flexing of each of the brackets tends to be localized to the segments or locations of the brackets having reduced cross sections. Several benefits are achieved thereby. The ease of manipulating an articulated dental model is enhanced, particularly protrusive movement. Flexing of the ends of the arms attendant the pivot means (34, 36) is reduced which ends to minimize inadvertent disengagement of the pivot means. Flexing of center section 92 is reduced and distortion of the sphere/base member junction is reduced. Webs 88, 90 still serve their primary purpose of reducing the load concentration attendant the junctions between the base member and the respective arms and yet readily accommodate flexing of the respective reduced cross section segments of the base member and attached arms.

In operation, as illustrated by arrows 110, 112, 114, in FIG. 10, the mounted casts may be relatively approached, separated, traversed, protruded, retracted, included and rotated through every possible condition and position of occlusal and masticatory registration by simple manipulation of flex the brackets of the articulator. The resiliently yieldable brackets accommodate all deviation from the initial position of the casts to the extent necessary to fully manifest the operative variations of position inherent in the natural dentures.

After fabrication of a restoration and fitting of same to the appropriate caste, the casts may be manipulated to trace the normal occlusal registration of the dentures as determined by the facet inclinations of the natural teeth and the operative correlation of the restoration with the condition to be redintegrated may be checked for correction and precise fitting. The restoration may be removed from the respective cast with or without physical severance of the casts from one another. By severing the brackets from one another at the pivot means, the casts readily become physically separated from one another and work on the restoration may become more facile. On completion of the work, the casts are rejoined to one another by rejoining the brackets at the pivot means. The severance capability, without an accompanying obligation or requirement to realign or even check the alignment of the casts, is of immense importance to the dental technician's efficiency. After severance, each cast may be worked on physically independent of the other and positioned upon or retained by a work surface which surface can support the cast at an orientation most favorable for the type and nature of the work to be done. And, a check of the accurancy of the work can be made in a matter of seconds by simply snapping the elements of the pivot means together to engage the two brackets with one another and then simulate and trace the paths of natural and masticatory registration.

While the principles of the invention have now been made clear in an illustrative embodiment, there will be immediately obvious to those skilled in the art many modifications of structure, arrangement, proportions, elements, materials and components, used in the practice of the invention which are particularly adapted for specific environments and operating requirements without departing from those principles.

I claim:

1. An articulator for correlating the casts of a dental model, each of the casts including a mounting, said articulator comprising in combination:
   (a) a pair of resiliently flexible brackets, each said bracket terminating at one end;

(b) means for pivoting the one end of one bracket with the one end of the other bracket about a common pivot axis;
(c) means for interconnecting each of the casts with another end of one bracket of said pair of brackets, said interconnecting means including a ball and socket joint and wherein one of the ball and socket of said ball and socket joint is defined by the mounting and wherein the other of the ball and socket of said ball and socket joint is formed by said bracket;
(d) a groove formed within a surface of said ball and socket joint; and
(e) each bracket of said pair of brackets including a base member having opposed ends and a pair of arms, each arm of said pair of arms depending from one of said opposed ends to form a junction therebetween, each of said opposed ends and each of said arms having a reduced cross section at the respective one of said junctions for encouraging flexing of each bracket of said pair of brackets at said junctions and a web disposed at each of said junctions for interconnecting the respective ones of said opposed ends and said arms for discouraging flexing in the plane of said webs;
whereby, flexing of the brackets at each of said junctions is encouraged after the angular relationship between each cast and the interconnected one of said pair of brackets has been fixed after registration of the casts relative to one another and during correlation of the casts.

2. The articulator as set forth in claim 1 wherein said groove extends partially circumferentially about said ball.

3. The articulator as set forth in claim 1 wherein said groove is developed in the surface of said ball of said ball and socket joint attendant each bracket of said pair of brackets.

4. An articulator for correlating the casts of a dental model, each of the casts including a mounting, said articulator comprising in combination:
(a) a pair of resiliently flexible brackets, each said bracket terminating at one end;
(b) means for pivoting the one end of one bracket with the one end of the other bracket about a common pivot axis;
(c) means for interconnecting each of the casts with another end of one bracket of said pair of brackets, said interconnecting means including a ball and socket joint and wherein one of the ball and socket of said ball and socket joint is defined by the mounting and wherein the other of the ball and socket of said ball and socket joint is formed by said bracket, said ball of each said ball and socket joint extends from each bracket of said pair of brackets from a point intermediate said opposed ends;
(d) a groove formed within a surface of said ball and socket joint; and
(e) each bracket of said pair of brackets including a base member having opposed ends and a pair of arms, each arm of said pair of arms depending from one of said opposed ends to form a junction therebetween, each of said opposed ends and each of said arms having a reduced cross section at the respective one of said junctions for encouraging flexing of each bracket of said pair of brackets at said junctions and web disposed at each of said junctions for interconnecting the respective ones of said opposed ends and said arms for discouraging flexing in the plane of said webs;
whereby, flexing of the brackets at each of said junctions is encouraged after the angular relationship between each cast and the interconnected one of said pair of brackets has been fixed after registration of the casts relative to one another and during correlation of the casts.

5. The articulator as set forth in claim 4 wherein said groove extends partially circumferentially about said ball.

6. The articulator as set forth in claim 4 wherein both ends of said groove terminate in proximity to the respective bracket.

7. The articulator as set forth in claim 4 wherein said ball extends from and off center of said base member.

8. A method for mounting casts of a dental model to afford correlation of the casts throughout a full range of occlusal and masticatory registration, said method comprising the steps of:
(a) pivoting along a pivot axis one end of a first bracket with a hingedly connected one end of a second bracket;
(b) interconnecting the other end of one of the brackets through a pivot mechanism providing pivotal freedom between each cast and its connected bracket about any axis of a set of intersecting orthogonal axis, each pivot mechanism including one element of a ball and socket joint and another element of the ball and socket joint being disposed at the other end of each bracket, said step of interconnecting including the step of interconnecting the one and the other elements to form a ball and socket joint between each cast and its attached bracket;
(c) positioning the casts relative to one another at one end of the range of occlusal and masticatory registration to be reintegrated by adjusting the angular relationship about any or all pivot axis between each cast and its engaged bracket and by adjusting the angular relationship about the pivot axis between the hingedly connected ends of the brackets;
(d) immobilizing the pivot mechanism between each cast and its engaged bracket by applying and flowing the adhesive into a groove extending into each ball and socket joint on completion of said positioning step to maintain permanently fixed the angular relationship between each cast and its respective brackets; and
(e) encouraging flexing of each of the brackets primarily at specific locations of each of the brackets by having a reduced cross section at such specific locations to assist in the correlation of the casts throughout the full range of occlusal and masticatory registration.

9. The method as set forth in claim 8 wherein the groove is disposed in the ball of the ball and socket joint and wherein said step of flowing includes the step of introducing the adhesive into the groove of the ball to introduce flow of adhesive between opposed surfaces of the ball and socket joint.

10. A method for mounting casts of a dental model to afford correlation of the casts through a full range of occlusal and masticatory registration, said method comprising the steps of:
a. pivoting along a pivot axis one end of a first bracket with a hingedly connected one end of a second bracket;

b. interconnecting the other end of one of the brackets through a pivot mechanism providing pivotal freedom between each cast and its connected bracket about any axis of a set of intersecting orthogonal axis;

c. positioning the casts relative to one another at one end of he range of occlusal and masticatory registration to be reintegrated by adjusting the angular relationship about any or all pivot axis between cast and its engaged bracket and by adjusting the angular relationship about the pivot axis between the hingedly connected ends of the brackets;

d. immobilizing the pivot mechanism between each cast and its engaged bracket with an adhesive, said step of immobilizing includes the step of flowing the adhesive into a groove extending into the pivot mechanism, on completion of said positioning step to maintain permanently fixed the angular relationship between each cast and its respective brackets; and e. encouraging flexing of each of the brackets primarily at specific locations of each of the brackets by having a reduced cross section at such specific locations to assist in the correlation of the casts throughout the full range of occlusal and masticatory registration.

11. The method as set forth in claim 10 wherein each bracket includes a base member having a pair of opposed ends and an arm depending from each of the opposed ends to form a junction therebetween and wherein the cross section of the base member is reduced at the opposed ends and the cross section of each of the arms is reduced at the junction to carry out said step of encouraging flexing.

12. A method for reintegrating the casts of a dental model through a full range of occlusal and masticatory registration to develop a dental prosthetic device mounted on the casts, said method comprising the steps of:

(a) forming a mounting at each cast;

(b) pivoting along a pivot axis one end of a first bracket with a hingedly connected one end of a second bracket;

(c) interconnecting each mounting with the other end of one of the brackets through a ball and socket joint;

(d) positioning the casts relative to one another at one end of the range of occlusal and masticatory registration to be redintegrated by adjusting the angular relationship between each mounting and its engaged bracket and adjusting the angular relationship about the pivot axis between the hingedly connected ends of the brackets;

(e) immobilizing the ball and socket joint between connected ones of the mounting and the brackets with an adhesive, said step of immobilizing including the step of flowing the adhesive into a groove extending into each ball and socket joint, to maintain permanently fixed the angular relationship established between connected ones of the mountings and brackets on completion of said step of positioning;

(f) flexing the brackets to translate and rotate the casts relative to one another to determine adjustments necessary to the model teeth or prosthetic devices or restorations formed thereon;

(g) encouraging flexing of each of the brackets primarily at specific locations of each of the brackets by having a reduced cross section of the brackets at such specific locations to assist in the correlation of the casts throughout the full range of occlusal any masticatory registration;

(h) alteratively pivoting the casts about the pivot axis of the brackets through an obtuse angle or disengaging the brackets one from the other to permit unrestricted access to the cast for making the adjustments determined in said flexing step;

(i) alternatively repivoting the casts into registration with one another or reengaging the brackets with one another depending upon whether said pivoting or disengaging step, respectively, were undertake; and (j) repeating said steps of flexing, alternatively pivoting or disengaging and alternatively repivoting or reengaging until the model teeth, prosthetic device or restoration is developed.

13. The method as set forth in claim 12 wherein each of the brackets includes a base member having opposed ends and an arm depending from each opposed end at a junction formed therebetween which junctions define each of the specific locations and including the steps of restraining flexing in the plane defined by a web disposed at each of the junctions.

14. The method as set forth in claim 13 wherein said step of encouraging flexing comprises flexing along the base member at the opposed ends coincident with the length of the opposed ends which length is reduced in cross section.

15. The method as set forth in claim 13 wherein said steps of encouraging flexing comprises flexing along each of the arms coincident with the length of the arms from the respective junction which length is reduced in cross section.

16. The method as set forth in claim 15 wherein said step of encouraging flexing comprises flexing along the base member at the opposed end coincident with the length of the opposed ends which length is reduced in cross section.

17. The method as set forth in claim 16 wherein said step of encouraging flexing is graduated as a function of the taper of the reduction in cross section of each of the arms and base members.

18. The method as set forth in claim 12 wherein the ball of each ball and socket joint is grooved and wherein said step of flowing comprises the step of introducing the adhesive into the groove of each ball to induce flow of the adhesive between opposed surfaces of each ball and socket joint.

19. An articulator for correlating the casts of a dental model, each of the casts including a mounting, said articulator comprising in combination:

(a) a pair of resiliently flexible brackets, each said bracket terminating at one end;

(b) means for pivoting the one end of one bracket with the one end of the other bracket about a common pivot axis;

(c) means for interconnecting each of the casts with another end of one bracket of said pair of brackets, said interconnecting means including a ball and socket joint and wherein one of the ball and socket of said ball and socket joint is defined by the mounting and wherein the other of the ball and socket of said ball and socket joint is formed by said bracket;

(d) each bracket of said pair of brackets including a base member having opposed ends and a pair of arms, each arm of said pair of arms depending from one of said opposed ends to form a junction therebetween, each of said opposed ends and each of said arms having a reduced cross section at the respective one of said junctions for encouraging flexing of each bracket of said pair of brackets at said junctions, said reduced cross section of each of said arms is approximately square, the central portion of said base member intermediate said opposed ends is also approximately square in cross section, and a web disposed at each of said junctions for interconnecting the respective ones of said opposed ends and said arms for discouraging flexing in the plane of said webs, each of said webs is recessed from one side of said arms and said base member at the respective one of said junctions, also each of said webs is flush with another side of said arms and said base member at the respective one of the junctions;

(e) a groove formed within a surface of said ball and socket joint; and (f) fixing means disposed intermediate the ball and socket of each of said ball and socket joints for fixing the angular relationship therebetween;

whereby, flexing of the brackets at each of said junctions is encouraged after the angular relationship between each cast and the interconnected one of said pair of brackets has been fixed after registration of the casts relative to one another and during correlation of the casts.

20. The articulator as set forth in claim 19, wherein said groove extends partially circumferentially about said ball.

21. The articulator as set forth in claim 19, wherein said groove is developed in the surface of said ball of said ball and socket joint attendant each bracket of said pair of brackets.

22. An articulator for correlating the casts of a dental model, each of the casts including a mounting, said articulator comprising in combination:

(a) a pair of resiliently flexible brackets, each said bracket terminating at one end;

(b) means for pivoting the one end of one bracket with the one end of the other bracket about a common pivot axis;

(c) means for interconnecting each of the casts with another end of one bracket of said pair of brackets, said interconnecting means including a ball and socket joint wherein one of the ball and socket of said ball and socket joint is defined by the mounting and wherein the other of the ball and socket of said ball and socket joint is formed by said bracket, said ball of each said ball and socket joint extends from each bracket of said pair of brackets from a point intermediate said opposed ends;

(d) fixing means disposed intermediate the ball and socket of each of said ball and socket joints for fixing the angular relationship therebetween;

(e) a groove formed within a surface of said ball and socket joint; and (f) each bracket of said pair of brackets including a base member having opposed ends and a pair of arms, each arm of said pair of arms depending from one of said opposed ends to form a junction therebetween, each of said opposed ends and each of said arms having a reduced cross section at the respective one of said junctions for encouraging flexing of each bracket of said pair of brackets at said junctions, the central portion of said base member intermediate said opposed ends is approximately square in cross section, and a web disposed at each of said junctions for interconnecting the respective ones of said opposed ends and said arms for discouraging flexing in the plane of said webs, each of said webs is flush with another side of said arms and said base member at the respective one of the junctions;

whereby, flexing of the brackets at each of said junctions is encouraged after the angular relationship between each cast and the interconnected one of said pair of brackets has been fixed after registration of the casts relative to one another and during correlation of the casts.

23. The articulator as set forth in claim 22, wherein said groove extends partially circumferentially about said ball.

24. The articulator as set forth in claim 22, wherein both ends of said groove terminate in proximity to the respective bracket.

25. The articulator as set forth in claim 22, wherein said ball extends from and off center of said base member.

* * * * *